United States Patent
Taniguchi et al.

(10) Patent No.: US 8,032,201 B2
(45) Date of Patent: Oct. 4, 2011

(54) MAGNETIC RESONANCE IMAGING DEVICE

(75) Inventors: Yo Taniguchi, Kokubunji (JP); Hisaaki Ochi, Kodaira (JP); Tetsuhiko Takahashi, Tokyo (JP); Masahiro Takizawa, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 774 days.

(21) Appl. No.: 11/917,689

(22) PCT Filed: Jun. 15, 2006

(86) PCT No.: PCT/JP2006/312023
§ 371 (c)(1),
(2), (4) Date: Dec. 14, 2007

(87) PCT Pub. No.: WO2006/135003
PCT Pub. Date: Dec. 21, 2006

(65) Prior Publication Data
US 2009/0030302 A1    Jan. 29, 2009

(30) Foreign Application Priority Data

Jun. 15, 2005   (JP) ................................. 2005-174489
Apr. 5, 2006    (JP) ................................. 2006-103729

(51) Int. Cl.
A61B 5/05   (2006.01)
(52) U.S. Cl. ....................... 600/410; 382/128; 382/130
(58) Field of Classification Search .................. None
See application file for complete search history.

(56) References Cited

U.S. PATENT DOCUMENTS 5,924,987 A    7/1999  Meaney et al.
2004/0057633 A1 *    3/2004  Mai et al. ................... 382/284

* cited by examiner

*Primary Examiner* — Long V. Le
*Assistant Examiner* — Nicholas Evoy
(74) *Attorney, Agent, or Firm* — Antonelli, Terry, Stout & Kraus, LLP.

(57) ABSTRACT

The magnetic resonance imaging apparatus includes a control unit for controlling a pulse sequence that applies an RF magnetic field and a magnetic field gradient to a subject placed in a static magnetic field and detects a magnetic resonance signal generated from the subject, and a calculation unit for processing the signal, and the control unit performs the process including the steps of; (1) obtaining first images at different positions in a first direction, (2) obtaining images after the first images are subjected to correction of brightness distortion, (3) obtaining images after the images as to which the brightness distortion has been corrected are further subjected to correction of positional distortion, and (4) synthesizing by a weighting calculation, overlapping areas of the images, after the positional distortion thereof has been corrected. According to this magnetic resonance imaging apparatus, the positional distortion and the brightness distortion can be corrected upon connecting the images, in the multi-station imaging.

11 Claims, 12 Drawing Sheets a
b
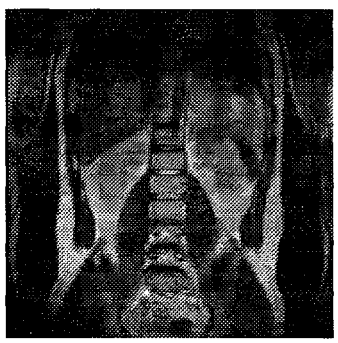
1
2
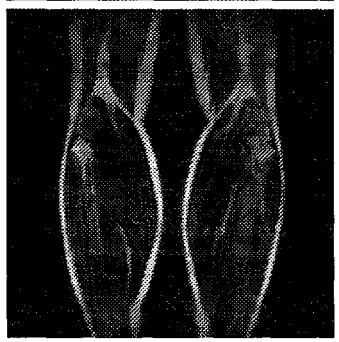
3
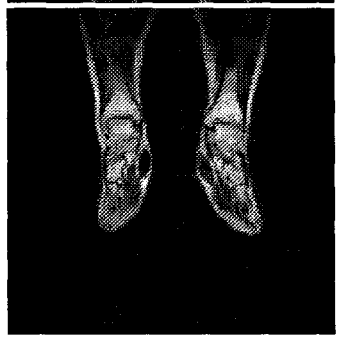
4
FIG. 2

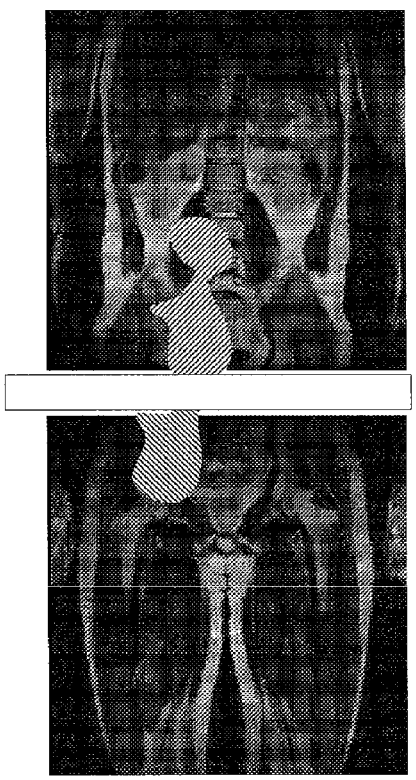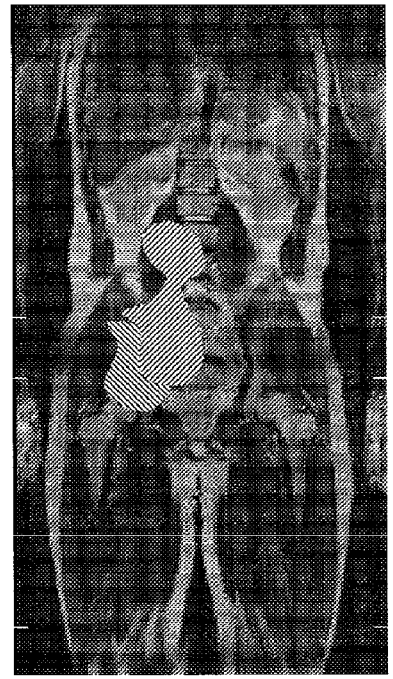
FIG. 10

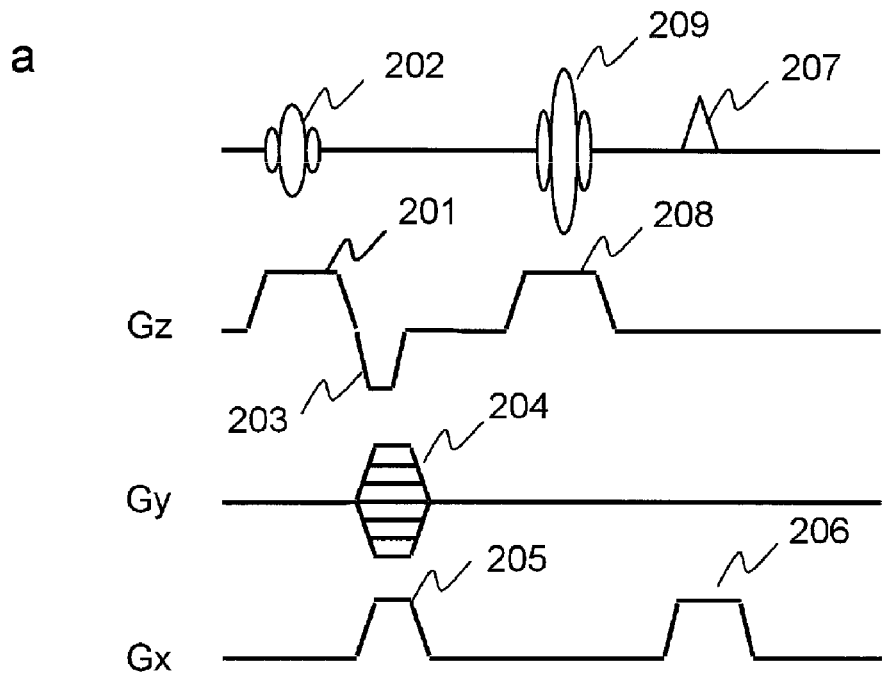
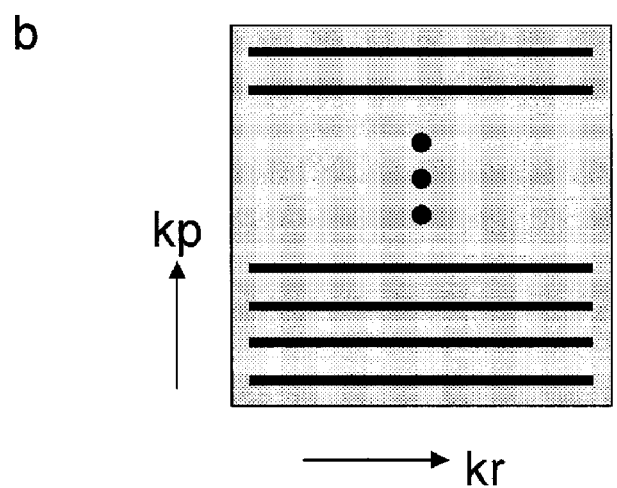
FIG. 12

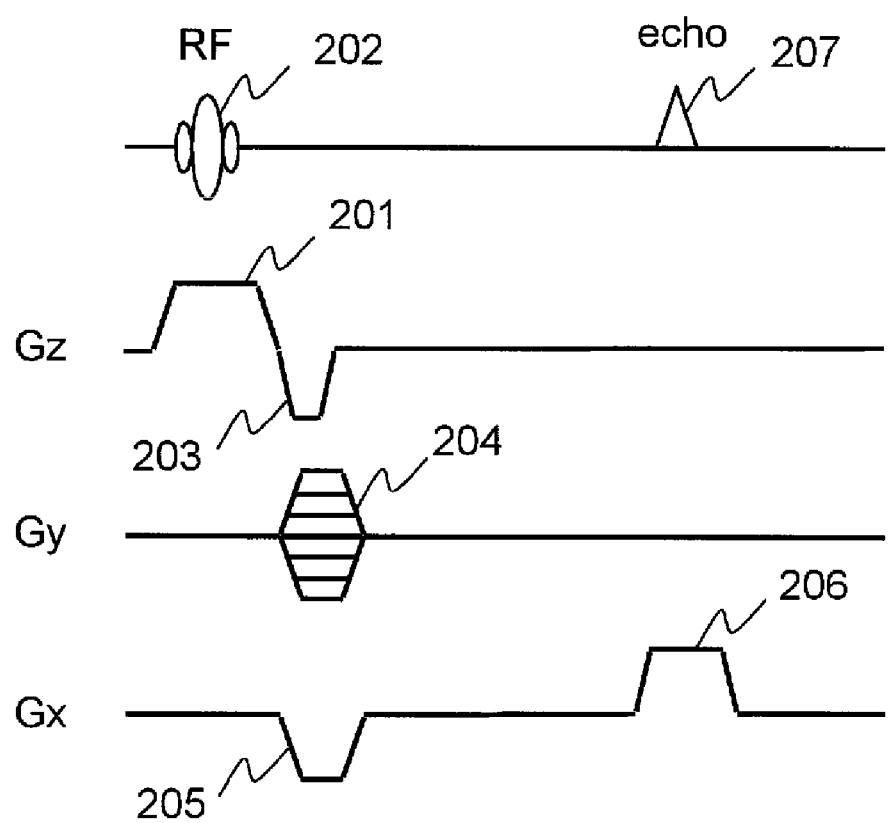
F I G. 1 3

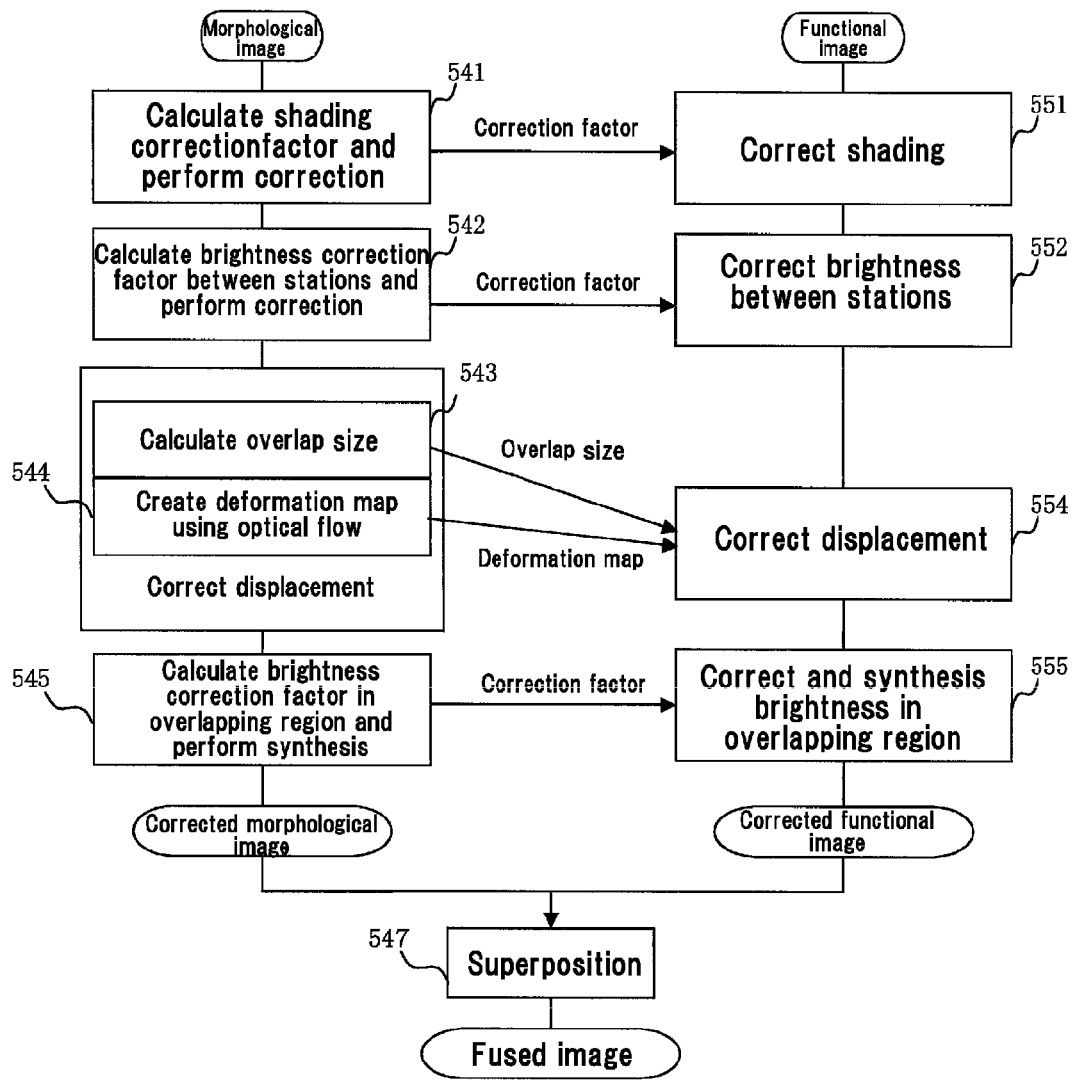
F I G. 1 4

FIG. 15

MAGNETIC RESONANCE IMAGING DEVICE

TECHNICAL FIELD

The present invention relates to a magnetic resonance imaging technique.

BACKGROUND ART

A magnetic resonance imaging (MRI) apparatus is a medical image diagnostic apparatus that applies an RF magnetic field and a magnetic field gradient to a subject placed in a static magnetic field, and measures a signal generated from the subject according to a nuclear magnetic resonance, so that an image is created. In the MRI apparatus, a size of an area that can be a target for imaging at one time is limited to around 40 cm. This is because a homogeneous region of the static magnetic field has a shape of sphere with a diameter of around 45 cm. Therefore, if there is a requirement to take an image of wider area such as imaging a whole body, it is necessary that the imaging area is divided for the imaging of multiple times, and obtained images are connected (see the patent document 1, for example). This is referred to as multi-station imaging. In order to connect the images, when each of the images are taken without any overlapping, the images are simply arranged side by side, whereas when there is an overlapping part between each of the images, the overlapping part is weighted-averaged so as to synthesize an image.

In the meantime, images taken by the MRI includes a morphological image where an internal structure of the subject is reflected onto a brightness distribution, and a functional image where an active state of an imaging target is reflected onto the brightness distribution. Since the functional image is obtained by imaging the functions, generally it is hard to say that the structure is sufficiently extracted. Moreover, in many cases, spatial resolution tends to be low due to a difficulty in imaging. Considering the problems above, in order to figure out an accurate position of the functional information being acquired, the functional image is often displayed with a morphological image that is separately taken, superimposing one on another.

[Patent Document 1]
U.S. Pat. No. 5,924,987

DISCLOSURE OF THE INVENTION

Problem to be Solved by the Invention

An image of an MRI has a problem that positional distortion and brightness distortion at a location are likely to become higher, as the location is closer to the periphery of a field of view (FOV), and magnitude of the distortion may be different depending on the location. With the distortion as such, when images of respective stations are connected for imaging of a wide area as described above, there has been a problem that displacements or brightness unevenness may occur at a joint on the composite image. This problem causes a major impediment for giving a diagnosis. Furthermore, even in the case where multiple images include distortions different in locations or different in brightness, a morphological image, on which a structure of the imaging target is reflected in detail, is capable of visibly figuring out association between the image and the structure in many cases. On the other hand, as for a functional image, such distortions may make it difficult to figure out the association between images, because the functional image is generally low in spatial resolution and the structure is not sufficiently depicted.

Furthermore, a direction and magnitude of the positional distortion are determined by imaging parameters, and in general, it is different between the morphological image and the functional image. Therefore, if the morphological image and the functional image are superimposed on one another as they are, it has been a problem that there occur a displacement therebetween.

A first object of the present invention is to provide a magnetic resonance imaging apparatus in which the positional distortion and the brightness distortion can be corrected, when images are connected in the multi-station imaging. A second object of the present invention is to provide a magnetic resonance imaging apparatus in which the positional distortion and the brightness distortion of a morphological image and a functional image are corrected, so that there is no positional distortion and brightness distortion in the composite image, in the multi-station imaging.

Means to Solve the Problem

An MRI apparatus according to the present invention for achieving the first object includes an imaging means for applying an RF magnetic field and magnetic field gradients to a subject placed in a static magnetic field and for detecting a magnetic resonance signal generated from the subject, a calculation means for processing the signal, and a control means for controlling the imaging means and the calculation means, wherein, the control means exercises control to perform a process including the steps of;

(1) obtaining first images at different positions in a first direction, (2) obtaining images by correcting brightness distortion of the first images, (3) obtaining images by correcting positional distortion of the images as to which the brightness distortion has been corrected, and (4) synthesizing by a weighting calculation, overlapping areas of the images as to which the positional distortion has been corrected.

The MRI apparatus according to the present invention to achieve the second object includes, a means for generating a static magnetic field, a means for generating an RF pulse to be applied to a subject that is placed in the static magnetic field, a means for generating a magnetic field gradient that is superimposed on the static magnetic field, a table member for placing the subject, a first imaging means for acquiring multiple morphological images respectively corresponding to multiple positions in the longitudinal direction of the table member, a second imaging means for acquiring multiple functional images respectively corresponding to multiple positions in the longitudinal direction of the table member, a correction means for calculating brightness distortion corrective information and positional distortion corrective information as to the morphological image, and for correcting brightness distortion and positional distortion of the functional image, by using the brightness distortion corrective information and the positional distortion corrective information, respectively, a display means for displaying the functional image being corrected, and a control means for controlling the first imaging means, the second imaging means, and the correction means.

Effect of the Invention

According to the present invention, the images are connected after the positional distortion and the brightness distortion of the images have been corrected. Therefore, it is possible to obtain an image without any displacements or brightness unevenness at the joint of the images after being connected. In addition, since the correction of the brightness distortion is performed before correcting the positional distortion, the positional distortion can be corrected with a high accuracy.

According to the present invention, the positional distortion and the brightness distortion of the morphological image and the functional image are corrected, by using the corrective information for the positional distortion and brightness distortion as to the morphological image. Therefore, it is possible to obtain a composite image without any displacement in position and brightness, even when the morphological image and the functional image are superimposed one on another, and in addition, when the images are connected in the multi-station imaging.

BRIEF DESCRIPTION OF THE DRAWINGS

FIG. 2 illustrates images of each station and a conventional image synthesis;

FIG. 10 illustrates a morphological image and a functional image of each station, and a conventional image synthesis;

FIG. 12 illustrates SE in an embodiment of the present invention;

FIG. 13 illustrates GE in an embodiment of the present invention;

FIG. 14 is a flowchart for synthesizing images in an embodiment of the present invention; and FIG. 15 illustrates a result obtained by applying the present invention.

BEST MODE FOR CARRYING OUT THE INVENTION

Figure 1:
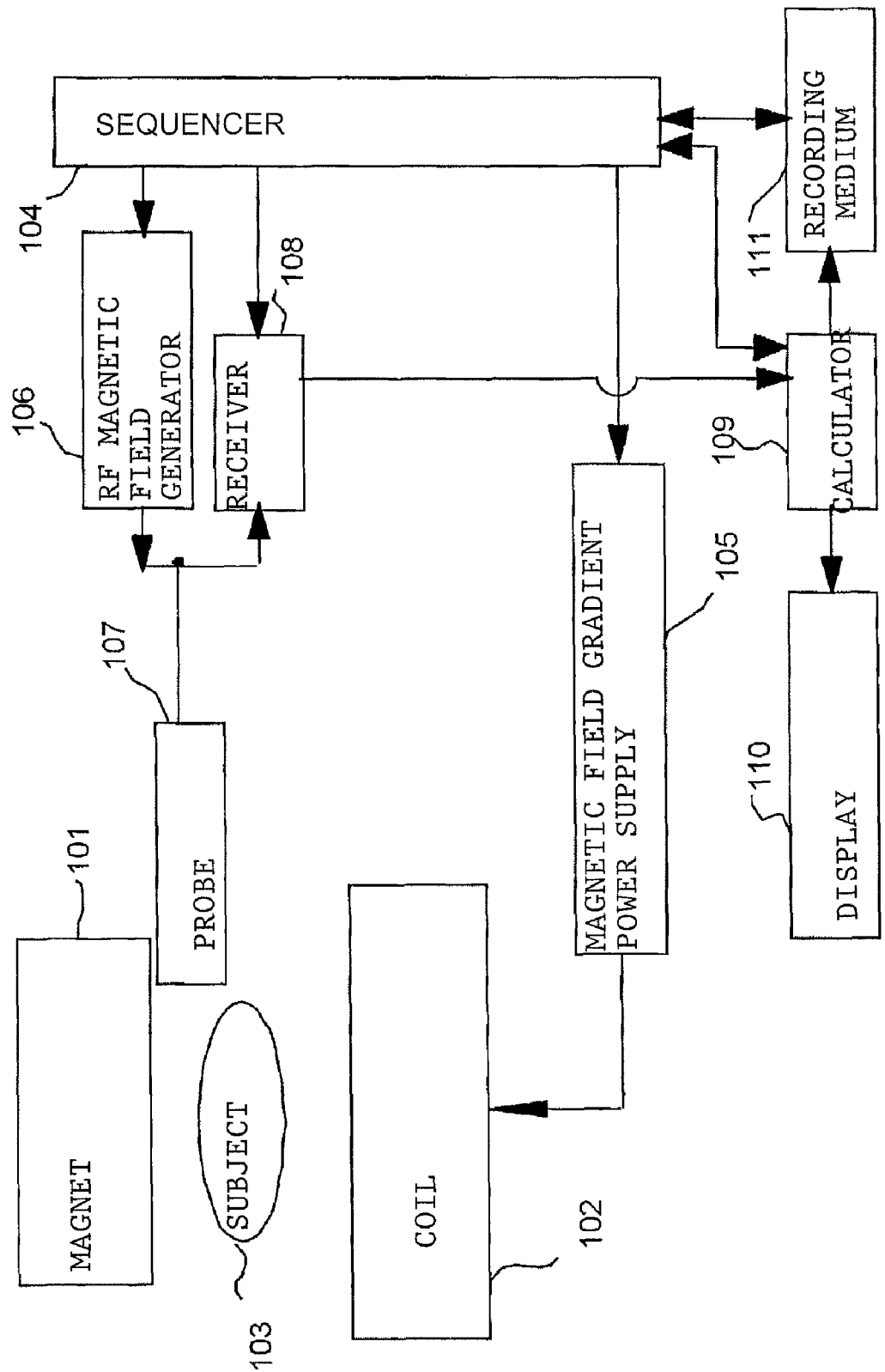
FIG. 1 illustrates a configuration example of the MRI apparatus to which the present invention is applied.

Hereinafter, an embodiment of the present invention will be described in detail with reference to the accompanying drawings. FIG. 1 is a block diagram showing a schematic configuration of an MRI apparatus to which the present invention is applied. This MRI apparatus is provided with a magnet 101 for generating a static magnetic field, a coil 102 for generating magnetic field gradients, a sequencer 104, a magnetic field gradient power supply 105, an RF magnetic field generator 106, a probe 107 for irradiating an RF magnetic field and detecting a nuclear magnetic resonance signal, a receiver 108, a calculator 109, a display 110, a recording medium 111, and the like. A subject (for example, a living body) 103 is installed on a bed (table) within a static magnetic field space generated by the magnet 101. The sequencer 104 transmits a command to the magnetic field gradient power supply 105 and the RF magnetic field generator 106 to generate magnetic field gradients and an RF magnetic field, respectively. The RF magnetic field is applied to the subject 103 via the probe 107. Signals generated from the subject 103 are received by the probe 107, and then, they are detected by the receiver 108. A nuclear magnetic resonance frequency used as a reference of the detection (hereinafter, referred to as "detection reference frequency") is set by the sequencer 104. The thus detected signals are transmitted to the calculator 109, and the signals are subjected to a processing such as an image reconstruction here. The result is displayed on the display 110. If required, the signal being detected or a measurement condition may be stored in the storage medium 111.

The sequencer 104 generally exercises control so that each of the elements above operates at a timing and strength previously programmed. Among these programs, a program particularly describing the timing and strength of the RF magnetic field, the magnetic field gradients, and the signal receiving is referred to as "pulse sequence". As the pulse sequence, though it is not particularly limited, an SE pulse sequence such as spin echo (SE) and high-speed spin echo, a gradient echo (GE) pulse sequence, and echo planar spectroscopic imaging (EPSI), or the like, is provided.

Next, a first embodiment of an image forming method according to the aforementioned MRI apparatus will be explained. In the present embodiment, there will be explained a case where the imaging is performed by a multi-station imaging system. The multi-station imaging system is used when a field of view (FOV) is larger than an imaging available area, such as imaging of a whole body. According to this system, an image is taken after dividing the whole body into areas (stations), and images of respective stations are synthesized to produce a whole body image. Here, one example will be explained, that is, under the condition that the FOV of one-time imaging is set to 42 cm and the imaging is performed at every movement of the table by 35 cm, four times of imaging in total are performed with three times of table movement.

FIG. 2 illustrates images that are taken by using the high-speed spin echo imaging with 256×256 pixels. FIG. 2a illustrates four images from the shoulder to the feet of a human, and FIG. 2b is a resulting image obtained by synthesizing these four images, only using a weighted mean. Overlap size corresponds to (FOV−Moved distance)/FOV×256=43 pixels.

As shown in FIG. 2b, if the images are simply weighted-averaged, it is found that there are problems as the followings; the brightness levels are not consistent in the images of each station (in particular, the image at the third station is brighter than the others), the brightness of the overlapping area is degraded, and displacement in structures occurs in the overlapping area.

The present inventors have discussed that the problems above are caused mainly by the following: Inconsistency of the brightness level in each image of each station would be caused by that the images in respective stations are taken by different receiving coils and that the imaging parameter is adjusted independently so that the SN ratio in imaging is maximized with respect to each station.

The brightness in the overlapping area is degraded, because generally in the MRI, sensitivities of sending and receiving coils are lowered on the periphery of the FOV, and the brightness on the peripheral area of the image of each station is apt to be degraded compared to the central area (this is referred to as "shading"). Therefore, if a weighted average is applied to this state, there may cause a shortage of brightness.

The displacement in structure occurs in the overlapping area, because there is a positional distortion due to nonlinearities of the magnetic field gradients and inhomogeneity of the static magnetic field. The positional distortion due to the nonlinearities of the magnetic field gradients are specific to device, but the positional distortion due to the static magnetic field inhomogeneity may depend on conditions in imaging, in addition to the device factor.

Figure 3:
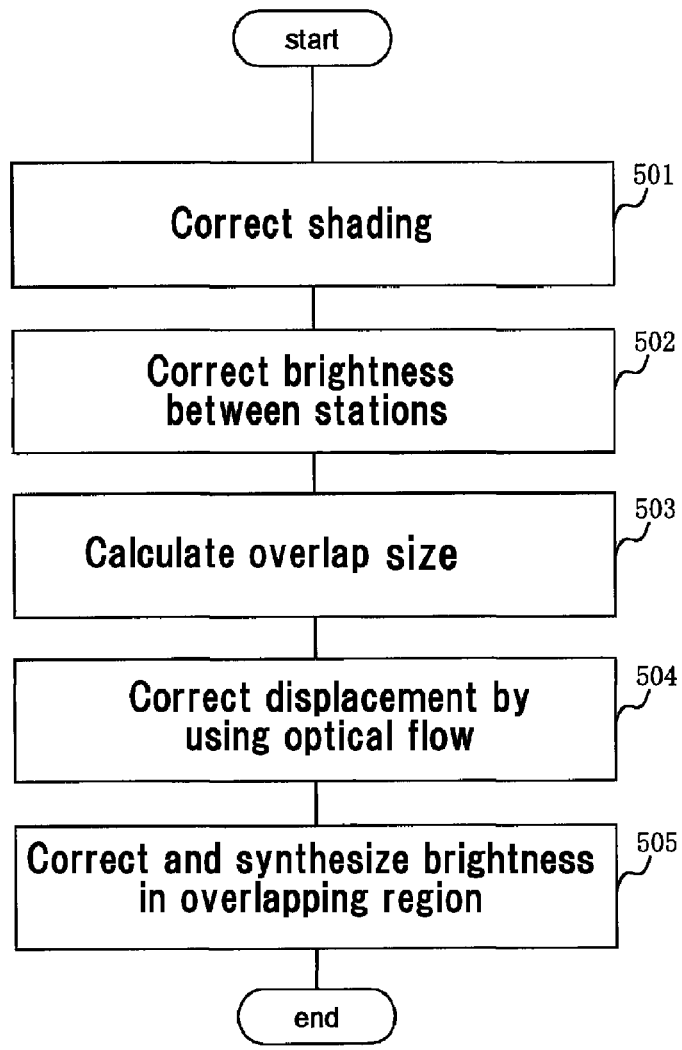
FIG. 3 is a flowchart for image synthesis according to an embodiment of the present invention.

According to the present embodiment, those problems above are solved by correcting images. FIG. 3 shows a flow of the correction process according to the present embodiment. Hereinafter, each step of the process will be explained.

Firstly, shading correction is performed in each station (step 501). Shading occurs mainly because the sensitivity distributions of the sending and receiving coils are degraded in the periphery of the FOV. For the correction, an image correction method as described in the Japanese unexamined patent application publication No. 7-222724 can be employed by way of example. In this method, a sensitivity distribution is found by applying a low-pass filter to an MR image or MR signal in advance, and a sensitivity correction factor of each pixel is obtained based on this sensitivity distribution. The sensitivity correction factor is provided with a value proportional to the inverse of sensitivity in a high sensitive area, and via the maximum value in a low sensitive area, a value to be the increasing function of the sensitivity in the extremely low sensitive area. A corrected image is obtained by multiplying an original image by the correction factor. In addition, if needed, a lowpass filter having a coefficient different by pixel is applied to the corrected image. With the processing above, the deterioration of brightness in the periphery of the FOV is almost resolved.

Next, the brightness correction is performed between the stations (step 502). In order to resolve the inconsistency of brightness between the stations, an average value of the brightness in the portion where the subject exists in each station (other than a noise area) is obtained, and correction is made to make the average values in the respective stations are equalized. In order to determine where the subject exists in each station, a predetermined threshold value is set, and a part where the brightness is equal to or more than the threshold value is determined as a part where the subject exists. As for the threshold value, it is necessary to calculate an optimum value with respect to each type of the image. However, according to a preliminary experiment, it is found that around 15% of the maximum brightness is preferable to be used as the threshold value. In the case where the brightness of an image in the station B is corrected with reference to an image in the station A, if the brightness of each pixel of the image B before correction is assumed as IB, the brightness after the correction is expressed by:

$$IB0=(IAm/IBm)\times IB=eIB \quad (1)$$

Here, $e(=IAm/IBm)$ represents the correction factor, and $IAm$ and $IBm$ represent brightness average values respectively in the image A and in the image B, the average values being obtained as to the area other than the noise area.

Next, a displacement in the overlapping amount (overlap size) between the stations is obtained (step 503). This displacement occurs because linearities of the magnetic field gradients are deteriorated in the periphery of the FOV, and the FOV is narrowed. Inherently, the overlap size between the stations can be calculated according to the FOV and a distance between the stations. In the example of FIG. 2, the overlap size corresponds to 43 pixels. However, the reconstructed image includes a positional distortion due to spatial nonlinearities of the magnetic field gradients and static magnetic field inhomogeneity. Therefore, the calculated value of overlap size is different from the overlap size of the reconstructed image.

Figure 4:
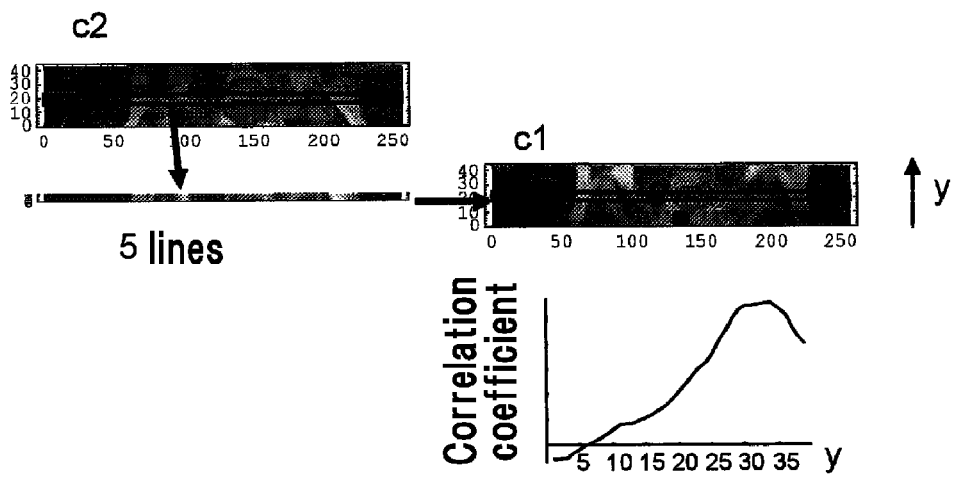
FIG. 4 is an explanatory view of calculation of an overlap size according to an embodiment of the present invention.

Therefore, with respect to the calculated value, a displacement therefrom is found. FIG. 4 shows a way how to find the displacement. The overlapping areas of the adjacent stations 1 and 2 are respectively assumed as c1 and c2, and a central part of the area c2 is taken out to calculate a correlation coefficient with respect to the y-direction of the area c1. Then, a position where the correlation coefficient becomes the maximum is found. When the position where the correlation coefficient becomes the maximum is assumed as r, and the calculated value of overlap size is assumed as n0, the overlap size of the reconstructed image is obtained by the integer part of $r(n0+4)/2$. In the image shown in FIG. 2, the calculated value of overlap size corresponds to 43 pixels (lines). Five lines in the central part of the overlapping area c2 (256×43 pixels) of the station 2 were taken out, and the correlation coefficient was calculated with respect to the y-direction of c1. A result of this calculation indicates that the position where the correlation coefficient becomes the maximum is 34, and the overlap size of the reconstructed image ($r(n0+4)/2$) is 57. Since the correlation coefficient is affected by a shape of the subject, SN ratio of the image, and the like, it is preferable to employ an average value of the overlap sizes that are obtained between the stations as to the entire stations and entire slices. In the image of FIG. 2, the overlap size was calculated as 55 pixels. It is to be noted that the processing above may be omitted if the displacement of the overlap size between the stations is small. It is because when the overlap size between the stations is small, it may be corrected simultaneously with correction of the displacement, which will be explained below.

Figure 5:
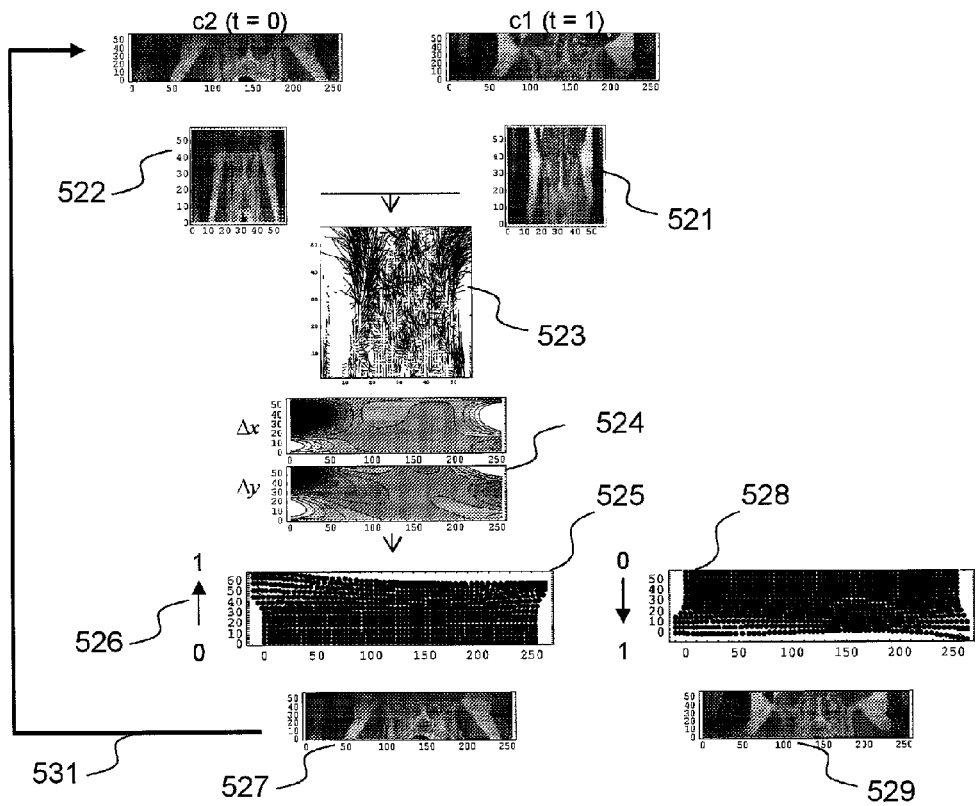
FIG. 5 is an explanatory view of correction of positional distortion according to an embodiment of the present invention.

Next, the displacement in the overlapping area is corrected (step 504). By using that the overlapping exists between the station images, a displacement volume between the images is calculated, so that the distortion is corrected. FIG. 5 shows an overview of the processing. FIG. 5 shows, by way of example, a case where the displacement volume is calculated using the images c1 and c2 (256×55), which are the overlapping parts respectively in the station 1 (head side) and in the station 2 (legs side). For calculating the displacement volume, the two images being overlapping are assumed as moving pictures of two frames, and an optical flow is utilized. However, since the optical flow cannot be obtained properly in the area with a low brightness, it is necessary to calculate the optical flow as to only an area where the subject exists. Therefore, for instance, assuming 15% of the maximum brightness of the overlapping area as a threshold value, it is determined that the subject exists in an area where the brightness is equal to or higher than this threshold value. This threshold value is required to be adjusted so that an optimum result can be obtained, depending on a type of the image as a target.

Firstly, the image c1 and image c2 of the overlapping parts are subjected to Fourier filtering to obtain the images with low resolution, 521 and 522. Next, by using the images with low resolution 521 and 522, an optical flow is calculated (step 523). It is optionally decided to what degree the resolution is made lower, but generally, it is preferable to reduce the resolution to approximately one quarter the original on each side. In the example being illustrated, the resolution is set to be around 32×16 pixels.

Each vector of the obtained optical flow indicates a moving amount of each pixel to transform the image c2 into the image c1. It is to be noted, however, that these vectors may include an improper value due to a noise effect, and further, the optical flow is not obtained as to the area where the brightness is low even though the subject exists in the area. On the other hand, it is normal that the displacement due to nonlinearities of the magnet field gradients or the static magnetic field inhomogeneity varies smoothly with respect to the space. Therefore, x component and y component of each vector are respectively expanded in advance by a homogeneous function of the third degree or less, using the least square method (step 524).

Figure 6:
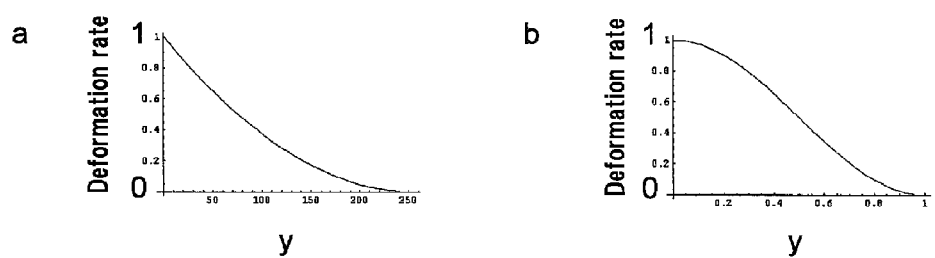
FIG. 6 illustrates a deformation ratio according to an embodiment of the present invention.

According to this function, a deformation map 525 is calculated, which represents a moving amount of each pixel, so that c2 agrees with c1. Here, if all the pixels in c2 are deformed homogeneously, the boundary between c2 and non-overlapping part in the station 2 becomes discontinuous. In order to handle this situation, when the deformation map is created, it is multiplied by a deformation ratio 526 that is related to a distance from the boundary. The deformation ratio is a function that becomes zero at the boundary portion, and it becomes one in an area that is the farthest from the boundary. By way of example, the function may be quadratic function as shown in FIG. 6a, or Hanning function as shown in FIG. 6b. According to this deformation map 525, c2 is deformed and an image 527 is obtained.

The processing above is also conducted for the case where c1 is deformed into c2, and its deformation map 528 is obtained. Then, c1 is deformed and an image 529 is obtained.

Under normal conditions, the positional distortion is corrected by the above processing, and with the subsequent brightness synthesis (step 505) an image without any distortion can be obtained. However, if a sufficient accuracy cannot be obtained after the correction just one-time, the correction process may be repeated while changing the resolution upon calculating the optical flow, for the images 527 and 529 to which the deformation map has been applied (step 531). The second correction processing may be performed at a resolution twice as high as the first time (64×32 pixels). According to the procedure above, relatively large displacement can be corrected by the first correction to correct, and more accurate correction can be made by the second correction.

Figure 7:
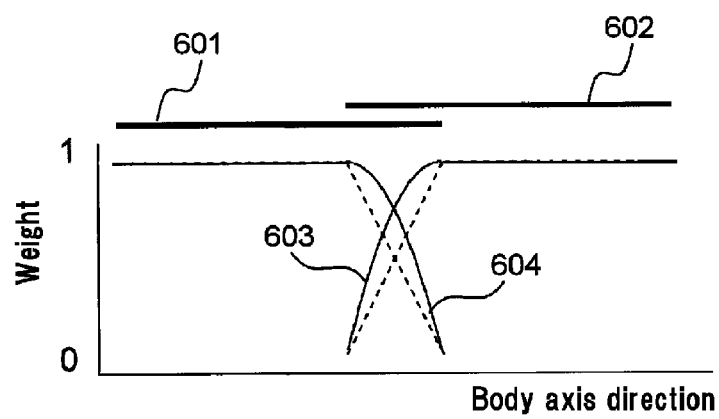
FIG. 7 is an explanatory view of a brightness correction and image synthesis according to an embodiment of the present invention.

Finally, the brightness synthesis is performed so that the brightness unevenness may not occur in the overlapping area, and a total image is created (step 505). If a general weighted-average is employed for synthesizing the overlapping areas, the brightness is insufficient. Therefore, it is necessary to increase the brightness to some extent. FIG. 7 shows this processing. If the station A 601 and the station B 602 are synthesized, weights 603 and 604 in the overlapping area are assigned by the quadratic function, instead of the linear function indicated by the dotted line. Since a simple arithmetic mean may cause a deterioration of the SN ratio, a square root of square-sum is calculated using those weights. If the brightness of each pixel in the images in the stations A and B, respectively, is assumed as IA and IB, and the weights are assumed as a and b, the brightness after the synthesis is expressed as the following.

$$\sqrt{\{(aIA)^2+(bIB)^2\}} \quad (2)$$

Figure 8:
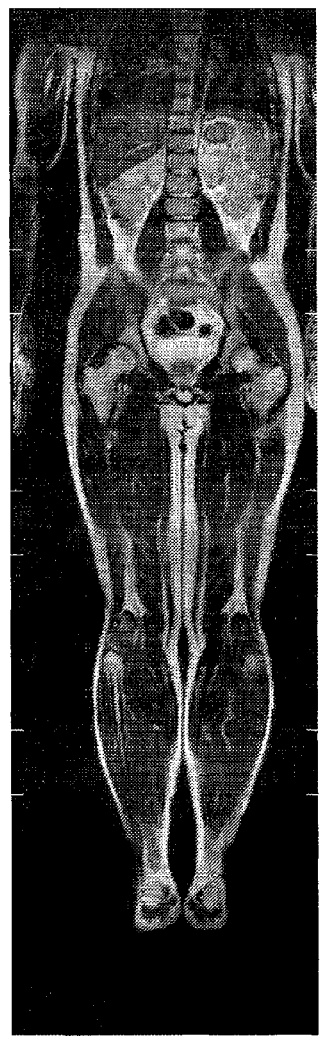
FIG. 8 illustrates a result obtained by applying the present invention.

FIG. 8 shows a result after all the processing steps described above have been applied to the image in FIG. 2. It is understood that the brightness unevenness and the structural displacement have been corrected.

The positional distortion and the brightness unevenness can be specified if a distortion specific to the device and an imaging condition are determined, and therefore, those distortion and unevenness may be corrected almost precisely. However, it is a complicated procedure to obtain a correction factor for each device or for each coil, and it is further difficult to cover all the limitless number of imaging conditions. In the present embodiment, the displacements and brightness disagreement between the stations can be corrected by using only the brightness information of the image in each station. Therefore, it features that implementation is easy and any maintenance is not required.

In the embodiment described above, a deformation map is obtained as to an area where the subject exists with respect to each individual overlapping area. However, some overlapping areas may include only a small area for the subject, and therefore, sufficiently accurate deformation map may not be obtained. In the case above, one deformation map obtained by averaging the optical flows in multiple overlapping areas may be used in common as a deformation map for all the overlapping areas. Processing as described above is possible, because each of the station images is taken at the same position within the MRI apparatus, and the positional distortion is approximately the same in any of the station images. Accordingly, a more accurate deformation map can be obtained, and stability in correcting the positional distortion is enhanced.

Next, a second embodiment of the present invention will be explained. In the present embodiment, corrective information obtained from a morphological image is used to correct brightness distortion and positional distortion of a functional image. Here, an explanation will be made, taking a diffusion-weighted image as an example of the functional image, in which a tumor can be highlighted. Cells in the tumor are densely arranged and the diffusion coefficient thereof is small compared to other tissues. Therefore, in the diffusion-weighted image, signals are measured at a higher level. By applying this method to a whole body imaging in multi-station, a whole body screening for finding a tumor is possible. A typical imaging method for imaging the diffusion-weighted image is the diffusion-weighted echo planar. In the diffusion-weighted image, however, most of the area other than the tumor generates a low signal. Therefore, it is not possible to correct the brightness distortion and the positional distortion by using the image information as described above.

In a normal diagnosis, it is rare to take only a functional image, and a morphological image is taken simultaneously in general. Only with the functional image, it is possible to determine whether or not there is a tumor, but it is difficult to determine in what part of the body the tumor is formed, because a part other than the tumor is hardly taken as an image.

Figure 9:
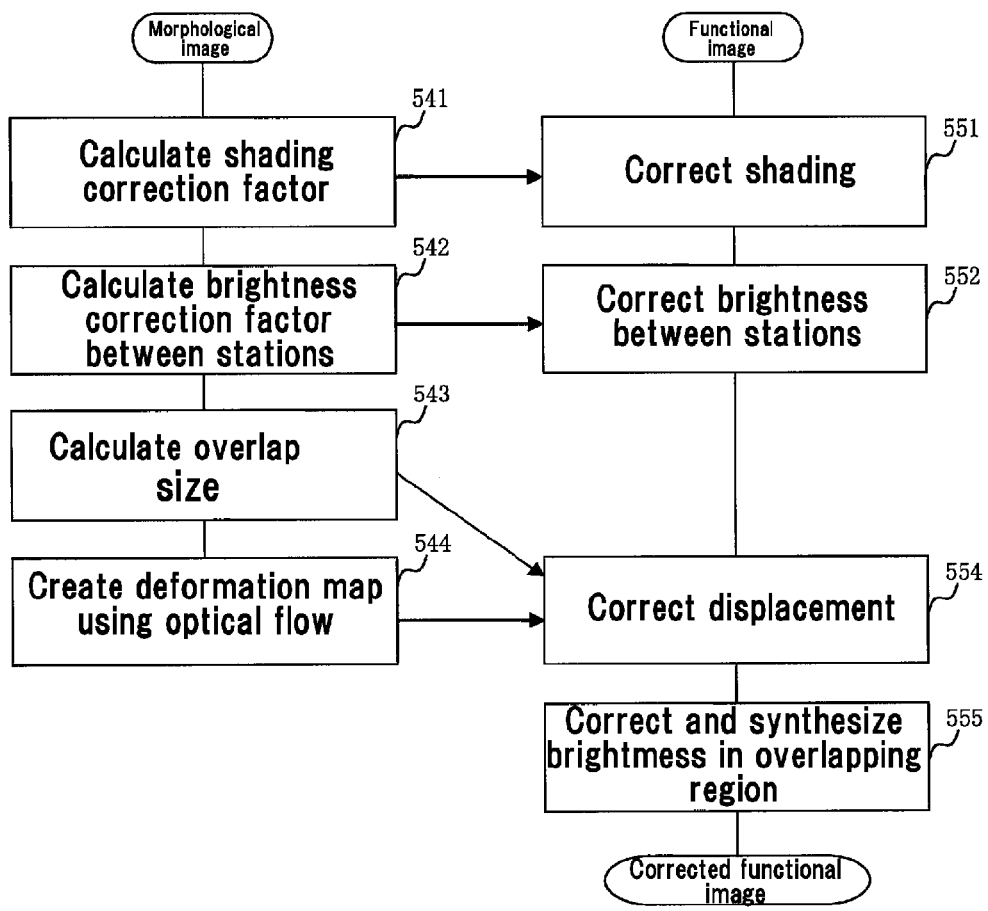
FIG. 9 is a flowchart for synthesizing images in an embodiment of the present invention.

Considering the situation above, in the present embodiment, corrective information for correcting the brightness distortion and the positional distortion is obtained by using a morphological image by which such information is easily acquired, and using the obtained corrective information, the functional image is corrected. An overview of the processing is shown in FIG. 9.

Firstly, a shading correction factor of each station image is calculated from the morphological image (step 541). The correction factor can be obtained in the same manner as step 501 (FIG. 3) in the first embodiment. The functional image in the same station is multiplied by the correction factor (step 551).

Next, an average value of brightness of the morphological image in the part where the subject exists (other than the noise area) in each station and the brightness correction factor e are obtained in the same manner as step 502 of the first embodiment (step 542). By using the brightness correction factor e, the functional image is corrected so that the brightness average value is made equal between the images of respective stations (step 552).

Next, similar to the step 503 and step 504 in the first embodiment, an overlap size between the stations is calculated from the morphological image (step 543), and simultaneously, a deformation map is created from the morphological image, by using an optical flow (step 544). Then, by using this deformation map, a displacement in the functional image is corrected (step 554). Finally, similar to the step 505, the correction and synthesis of brightness are performed in the functional image (step 554).

According to the present embodiment, since corrective information obtained from the morphological image is used, the functional image can be corrected with a high degree of accuracy. With the procedure above, it is possible to enhance diagnostic ability in whole body tumor screening.

Next, a third embodiment of the present invention will be explained. According to the present embodiment, positional distortion and brightness distortion in a functional image are corrected by using corrective information obtained from a morphological image, and this is the same as the second embodiment. In the present embodiment, however, by adjusting an imaging parameter, a displacement of the morphological image and that of the functional image are aligned. Firstly, an adjustment of the imaging parameter will be explained.

FIG. 10a shows a distribution of lactic acid imaged by the MRSI method by way of example, being displayed in color white with diagonally shaded, in such a manner as superimposed on the first image and the second image of FIG. 2. FIG. 10b shows an image obtained by synthesizing these images in the manner similar to FIG. 2. It is found that a displacement occurs even in the functional image. It is to be noted that the color of the functional image is white with diagonally shaded so as to help clearly showing the displacement, but actually, it is general to create color presentation so that a concentration distribution is identified.

Here, the brightness distortion is generally decided by the sensitivity distribution of the transmission and receiving probes as described above, and it hardly depends on a method of imaging. Therefore, it can be considered that the brightness distortion of the functional image is identical to that of the morphological image. On the other hand, since the positional distortion is generally changed by an imaging parameter, the functional image and the morphological image are taken, using the imaging parameter that makes the positional distortion in one image to agree with the positional distortion in the other image. Among the causes for the positional distortion, non-linearities of the magnetic field gradients are specific to a device, and it does not depend on a method of imaging. On the other hand, a positional distortion according to the static magnetic field inhomogeneity depends on the imaging parameter, the direction of the positional distortion corresponds to a readout direction, and the magnitude thereof is proportional to $\gamma \cdot \Delta H \cdot \Delta t$. Here, $\gamma$ represents a gyromagnetic ratio of an element, $\Delta H$ represents static magnetic field inhomogeneities, and $\Delta t$ represents a sampling rate. Therefore, if the imaging is performed under the condition that the static magnetic field inhomogeneities $\Delta H$ is constant, the magnitude of the positional distortion is equal as far as $\gamma \cdot \Delta t$ is kept constant even in a different imaging method. In the present embodiment, under the condition that the readout direction of the functional image is set to be the same as that of the morphological image, a product of the gyromagnetic ratio and the sampling rate is set to be equal in each element in imaging the functional image and the morphological image.

In order to explain the imaging parameter adjustment, an MRSI of lactic acid and a morphological image by the spin echo (SE) are taken as an example. FIG. 11a and FIG. 12a respectively show a pulse sequence of a high-speed imaging method (EPSI) being a method for the MRSI, and a pulse sequence of the spin echo method that is employed for taking the morphological image.

The EPSI method firstly applies a slice magnetic field gradient pulse 201 in the z-direction, together with irradiating an RF magnetic field (RF) pulse 202 having a proton resonance frequency fh, so as to excite the proton in a slice within the subject body. Then, a slice rephasing magnetic field gradient pulse 203, a phase encoding magnetic field gradient pulse 204 for adding positional information in the phase encoding direction (y-direction) to a magnetization phase, and a readout magnetic field gradient for dephasing 205 are applied, and thereafter, 180-degrees pulse 208 is irradiated. Then, while applying readout magnetic field gradient pulses 206, being positive and negative alternate for adding positional information in the readout direction (x), multiple magnetic resonance signals (echoes) 207 are measured. The above procedure from applying of the slice magnetic field gradient pulse to measuring of echoes is repeated every repetition time TR, and echoes required for obtaining one piece of image are measured. As shown in FIG. 11b, the echoes are arranged in the k-space and reconstructed by the three-dimensional Fourier transformation.

The SE method firstly applies the slice magnetic field gradient pulse 201 in the z-direction and irradiates an RF magnetic filed (RF) pulse 202 having a proton resonance frequency fh, so as to excite the proton in the slice within the subject body. Then, a slice rephasing magnetic field gradient pulse 203, a phase encoding magnetic field gradient pulse 204 for adding positional information in the phase encoding direction (y-direction) to a magnetization phase, and a readout magnetic field gradient for dephasing 205 are applied, and thereafter, a 180-degrees pulse 208 is irradiated. Then, while applying a readout magnetic field gradient pulse 206 for adding positional information in the readout direction (x) a magnetic resonance signal (echo) 207 is measured. The above procedure from applying of the slice magnetic gradient field pulse to measuring of echo is repeated every repetition time TR, and echoes required for obtaining one piece of image are measured. As shown in FIG. 12b, the echoes are arranged in the k-space and reconstructed by the two-dimensional Fourier transformation.

In the above two imaging methods, since an element as a target is the same proton, images each having the same positional distortion can be obtained in the respective methods, if the imaging is performed at an equal sampling rate in both methods. According to a principle of the MRI imaging, there is a relationship that $\gamma \cdot Gr \cdot Fov \cdot \Delta t = 1$. Here, Gr represents the strength in the readout magnetic field gradient pulse, and FOV represents a field of view. Therefore, if also the FOV is required to be the same between a morphological image and a functional image, Gr is also equalized therebetween.

Figure 11:
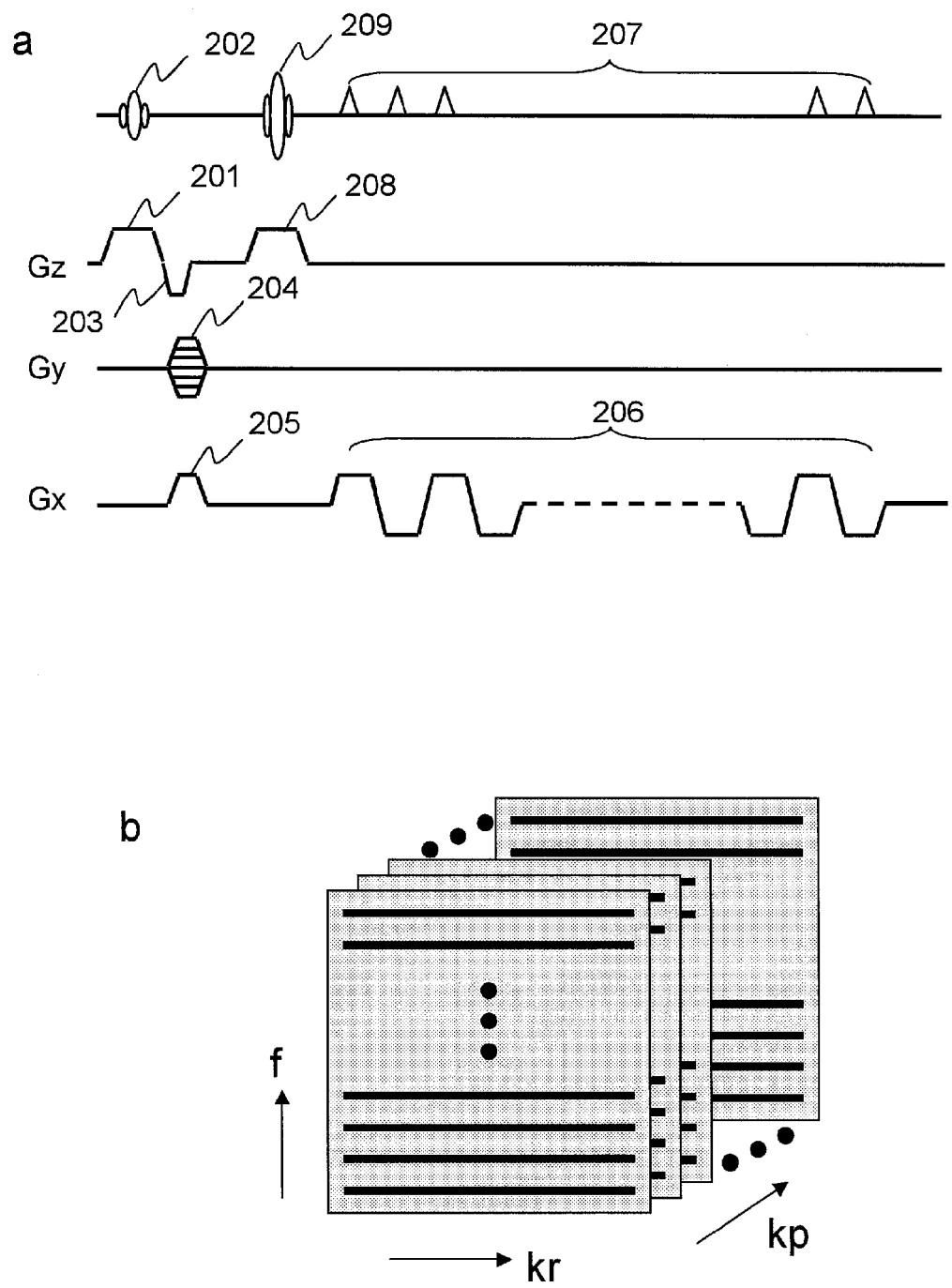
FIG. 11 illustrates EPSI in an embodiment of the present invention.

In the combination of the imaging methods shown in FIG. 11 and FIG. 12, there is also a case where saccharometabolism is measured by using $^{13}C$, instead of proton, as an element for the functional image. Here, the gyromagnetic ratio of the proton and that of the $^{13}C$ are respectively 42.58 MHz and 10.71 MHz, and therefore by setting the ratio of sampling rate to 1:3.98, in the imaging by the SE method and in the imaging by the EPSI, it is possible to obtain a morphological image and a functional image each having the same positional distortion.

As another example of the imaging parameter adjustment, there will explained a case where a blood vessel image taken by using $^{13}C$ contrast agent being hyperpolarized, and a morphological image are superimposed one on another. The proton contrast agent shows a large contrast difference compared to an area without the contrast agent, whereas the $^{13}$C contrast agent features that a signal can be obtained only from an area where the contrast agent exists.

An imaging method generally used for imaging by the use of the $^{13}$C contrast agent is a gradient echo method (GE). This pulse sequence is shown in FIG. 13. Firstly, the slice magnetic field gradient pulse 201 in the z-direction is applied and an RF magnetic field (RF) pulse 202 having a resonance frequency fc of $^{13}$C is irradiated, to excite $^{13}$C in the slice within the subject body. Then, a slice rephasing magnetic field gradient pulse 203, a phase encoding magnetic field gradient pulse 204 for adding positional information in the phase encoding direction (y-direction) to a magnetization phase, and a readout magnetic field gradient for dephasing 205, are applied. Thereafter, while applying a readout magnetic field gradient pulse 206 for adding positional information in the readout direction (x), a magnetic resonance signal (echo) 207 is measured. The above procedure from applying of the slice magnetic field gradient pulse to measuring of echoes is repeated every repetition time TR and echoes required for obtaining one piece of image are measured. Each of the echoes is arranged in the k-space and reconstructed by the two-dimensional Fourier transformation. It is to be noted here that an imaging time with respect to each image is 1.28 seconds, if an image of 128×128 pixels is taken assuming TR=10 ms, by way of example.

Here, it is considered a case where both a functional image of the $^{13}$C and a morphological image of the proton are taken according to this GE. Firstly, also in the GE method, the direction of the positional distortion corresponds to the readout direction. Therefore, the readout direction is set to be the same. In addition, the gyromagnetic ratio of the proton and that of the $^{13}$C are respectively 42.58 MHz and 10.71 MHz, and therefore, the ratio of sampling rate in the functional image and in the morphological image is set to 1:3.98. Accordingly, it is possible to obtain the morphological image and the functional image each having the same positional distortion.

The positional distortion and the brightness distortion in the same area of the morphological image and the functional image which are taken as described above, will be corrected as the following. FIG. 14 shows a flow of processing. The processing shown in FIG. 14 includes the steps having the same reference numbers as the steps in the second embodiment shown in FIG. 9, and the same processing is performed therein.

Specifically, a shading correction factor of each station is calculated as to the morphological image, and shading correction is performed (step 541). As described above, since the brightness distortion is almost the same between the morphological image and the functional image, the same correction factor obtained for the morphological image is also used for the functional image, and the shading correction is performed (step 551). As thus described, by using the sensitivity correction factor obtained using the morphological image to which a structure of the imaging target is fully reflected, it is possible to correct the shading of the functional image with a high degree of accuracy.

Next, brightness correction is performed between the stations (step 542). Specifically, an average value of the brightness other than a noise area is obtained as to the morphological image in each station, and a correction factor e is calculated with reference to a predetermined station image as a standard.

Generally, this brightness average value is obtained from all of each image. However, in the case where a brightness shading still remains in the overall image even after the shading correction (541), an influence of the brightness shading can be reduced by using the brightness average value of the overlapping area only or of the overlapping area with an area in proximity thereto only, and an accuracy in correcting the positional distortion thereafter can be improved.

It is also possible to obtain the correction factor e from the RF irradiation intensity and the sensitivity of probe as expressed by the formula (3).

$$e=(SA/HA)/(SB/HB) \quad (3)$$

Here, HA and HB represent the irradiation RF intensity when images A and B are taken respectively, SA and SB represent probe sensitivities when the images A and B are taken respectively. (SA/HA) and (SB/HB) represent relative sensitivities, when the images A and B are taken, respectively. The irradiation RF intensity is a value determined by adjusting the imaging parameter before the imaging, and the probe sensitivity is a value specific to the probe. This method is advantageous in that a processing is simplified compared to the method where the brightness average value is used. However, in the strict sense, the probe sensitivities slightly fluctuate depending on the subject, and therefore, its accuracy may be degraded to some extent.

Inconsistency of the brightness between the stations is almost the same in the morphological image and in the functional image. Therefore, it is possible to correct the functional image, also using the factor e that is identical to the factor obtained for the morphological image (step 552). By using the sensitivity correction factor obtained by using the morphological image to which a structure of the imaging target is fully reflected, shading of the functional image can be corrected with a high degree of accuracy.

Next, a displacement in overlap size between the stations is obtained (step 543). As explained in the first embodiment, a reference value n0 is calculated based on the FOV and the distance between the stations. Next, as shown in FIG. 4, a position r is found, which maximizes a correlation coefficient of the overlapping area of adjacent station images, and then, the displacement of the overlap size is calculated by using the reference value n0 and the position r having been calculated.

Next, a positional distortion in the overlapping area is corrected (step 544). Firstly according to the procedure shown in FIG. 5, a deformation map is created by using an optical flow. Images 521 and 522 are obtained by subjecting the images c1 and c2 of the overlapping part to a Fourier filtering and thereby lowering the resolution. Next, by using the images 521 and 522 with the lowered resolution, an optical flow is calculated (step 523). Each vector of the obtained optical flow indicates a moving amount of each pixel for transforming the image c2 into image c1. The x component and y component of each vector are respectively expanded in advance by a homogeneous function of the third degree or less, using the least square method (step 524). According to the function above, a deformation map 525 is calculated, which represents a moving amount of each pixel so as to coincide c2 with c1. When this deformation map is created, the quadratic function as shown in FIG. 6a, or Hanning function as shown in FIG. 6b are employed as the deformation ratio 526, and this ratio according to a distance from the boundary is used in multiplication. Following the deformation map 525 being calculated, c2 is transformed and an image 527 is obtained. Similarly, a deformation map 528 used when c1 is transformed into c2 is obtained, and an image 529 is acquired by transforming c1.

By using the overlap size and the deformation map thus obtained in step 543 and step 544, the positional distortion is corrected as to the functional image, similar to the morphological image (step 554). Since in many cases, the functional image does not reflect a structure of the imaging target enough to extract corrective information for the positional distortion, it may be difficult to extract sufficient information for correcting the positional distortion only by the functional image. In the present embodiment, similar to the second embodiment, by using the positional distortion corrective information (the overlap size and deformation map) which is obtained by using the morphological image to which a structure of the imaging target is fully reflected, it is possible to correct the positional distortion of the functional image with a high degree of accuracy. In the present embodiment, since the functional image and the morphological image are taken by using the imaging parameter which makes positional distortion in each image to be the same, it is possible to use the same positional distortion corrective information in both of the images. It is to be noted that if correction processing is repeated while changing the resolution in calculating the optical flow in step 544, multiple number of times of corrections are performed also for the functional image similarly.

Next, as to the morphological image, brightness synthesis is performed so that brightness unevenness may not occur in the overlapping area, and a total image is created (step 545). In the present embodiment, weights a and b of the quadratic function as shown in FIG. 7 and the aforementioned formula (2) are used for synthesis, and insufficient brightness is compensated. It is to be noted that as to the weights a and b, more appropriate value can be obtained by using the brightness value in the overlapping area and its periphery. For example, the weights a and b may be increased or decreased so as to equalize the brightness average values in the overlapping area and the brightness average values in the surrounding area after synthesizing images. Accordingly, even when the brightness unevenness cannot be corrected by the quadratic function, an optimum correction can be achieved. This brightness correction synthesis is also performed for the functional image by using the correction factor obtained from the morphological image in step 545 (step 555). Similar to the shading correction (step 551) and brightness correction (step 552) of the functional image, the brightness correction synthesis of the functional image can be done with a high degree of accuracy, by using the correction factor obtained from the morphological image.

Finally, the morphological image and the functional image, as to which the positional and brightness distortions are corrected, are superimposed one on another, and a composed (fused) image is created (step 547). Then, this composed image is displayed on the display.

FIG. 15 shows a result obtained by applying all the above processing to the images shown in FIG. 2 and FIG. 10. FIG. 15*a* is a result obtained by synthesizing only the morphological images, and FIG. 15*b* is a result obtained by synthesizing the morphological image and the functional image. It is understood that there are obtained the images as to which the brightness unevenness and the displacement in structure have been corrected. In addition, according to the aforementioned procedure, since corrective information obtained from the morphological image is used, the functional image can be corrected with a high degree of accuracy. Accordingly, a diagnostic ability for the whole body tumor screening can be enhanced, for instance.

In the present embodiment, similar to the aforementioned embodiment, it is possible to correct the positional distortion and brightness distortion between stations by using only the brightness information of the image in each station, and therefore, it features that implementation is easy and any maintenance is not required.

Also in the present embodiment, instead of obtaining the deformation map as to the area where the subject exists for each independent overlapping area, one deformation map can be used in common as the deformation map for all the overlapping areas, by calculating an average of optical flows in multiple overlapping areas. With the procedure above, even when the subject area is small and a deformation map having sufficient accuracy cannot be obtained, it is possible to obtain a deformation map having a high degree of accuracy, and therefore, stability in correcting the positional distortion can be improved.

What is claimed is:

1. A magnetic resonance imaging apparatus comprising:
   means for generating a static magnetic field;
   means for generating an RF pulse to be applied to a subject that is placed in the static magnetic field;
   means for generating a magnetic field gradient that is superimposed on the static magnetic field;
   a table member for installing the subject;
   first imaging means for acquiring multiple morphological images respectively according to multiples positions in the longitudinal direction of the table member;
   second imaging means for acquiring multiple functional images respectively corresponding to multiple positions in the longitudinal direction of the table member;
   correction means for calculating brightness distortion corrective information and positional distortion corrective information of the morphological images, and for correcting brightness distortion and positional distortion of the functional images, by using the brightness distortion corrective information and the positional distortion corrective information of the morphological images, respectively;
   display means for displaying the functional image being corrected; and
   control means for controlling the first imaging means, the second imaging means, and the correction means.

2. The magnetic resonance imaging apparatus according to claim 1, wherein,
   a readout direction of the morphological image and a readout direction of the functional image are identical, and
   a product of a gyromagnetic ratio of a target element and a sampling rate is equal in the functional image and the morphological image.

3. The magnetic resonance imaging apparatus according to claim 2, wherein,
   a strength of a readout magnetic field gradient pulse in the morphological image is equal to a strength of the readout magnetic field gradient pulse in the functional image.

4. The magnetic resonance imaging apparatus according to claim 1, wherein the control means is configured to perform the following steps:
   (1) obtaining first images at different positions in a first direction;
   (2) correcting brightness distortion of the first images;
   (3) correcting positional distortion of the images as to which the brightness distortion has been corrected; and
   (4) synthesizing by a weighting calculation, overlapping areas of the images as to which the positional distortion has been corrected.

5. The magnetic resonance imaging apparatus according to claim 4, wherein the step (2) further comprises the steps of:
   (2-1) calculating a shading correction factor for the first images, and obtaining images having been subjected to a shading correction; and
   (2-2) calculating a correction factor for correcting a difference in brightness level between the images that have been subjected to the shading correction, and obtaining images as to which the difference in brightness level has been corrected.

6. The magnetic resonance imaging apparatus according to claim 4, wherein the step (3) further comprises the steps of:
   (3-1) obtaining the positional distortion of the images, by using an overlapping area between the images as to which the brightness distortion has been corrected; and
   (3-2) obtaining images as to which the positional distortion has been corrected.

7. The magnetic resonance imaging apparatus according to claim 5, wherein
   the step (2-2) further comprises correcting the difference in brightness level, by using a brightness correction factor calculated from an irradiated RF intensity and a probe sensitivity.

8. The magnetic resonance imaging apparatus according to claim 6, wherein
   the step (3-1) further comprises obtaining the positional distortion of the images by using an optical flow of the overlapping area between the images.

9. The magnetic resonance imaging apparatus according to claim 8, wherein,
   the optical flow is obtained by averaging multiple optical flows in multiple overlapping parts between the first images acquired at different positions in the first direction.

10. The magnetic resonance imaging apparatus according to claim 1, wherein,
    the correction means further corrects the morphological image and the functional image by using the same positional distortion corrective information or the same brightness distortion corrective information.

11. The magnetic resonance imaging apparatus according to claim 1, wherein the display means further displays the functional image superimposed on the morphological image.

* * * * *